United States Patent
Cho et al.

(10) Patent No.: US 6,280,773 B1
(45) Date of Patent: Aug. 28, 2001

(54) OPTIMALLY STABILIZED MICROGRANULE COMPRISING 5-PYRROLYL-2-PYRIDYLMETHYLSULFINYLBENZIMIDAZOLE DERIVATIVE

(75) Inventors: Kil Do Cho; Dong Yeun Kim; Dong Woo Park, all of Seoul; Hong Ryeol Jeon, Suwon; Hee Jun Kim, Kwangmyung, all of (KR)

(73) Assignee: IL Yang Pharm. Co., Ltd., Kyungki-do (KR)

( * ) Notice: Subject to any disclaimer, the term of this patent is extended or adjusted under 35 U.S.C. 154(b) by 0 days.

(21) Appl. No.: 09/303,953

(22) Filed: May 3, 1999

(30) Foreign Application Priority Data

Dec. 29, 1998 (KR) .................................................. 98-60261

(51) Int. Cl.$^7$ ................ A61K 9/14; A61K 9/16; A61K 31/44
(52) U.S. Cl. ............ 424/489; 424/488; 424/494; 424/496; 514/338
(58) Field of Search ............... 514/338; 424/489, 424/494, 496, 488

(56) References Cited

U.S. PATENT DOCUMENTS

| | | |
|---|---|---|
| 2,540,979 | 2/1951 | Clymer et al. |
| 5,554,631 * | 9/1996 | Kim et al. ............... 514/338 |
| 5,703,097 * | 12/1997 | Kim et al. ............... 514/338 |

FOREIGN PATENT DOCUMENTS

| | | |
|---|---|---|
| 1 485 676 | 9/1977 | (GB). |
| WO 85/03436 | 8/1985 | (WO). |

* cited by examiner

*Primary Examiner*—Thurman K. Page
*Assistant Examiner*—Blessing Fubara
(74) *Attorney, Agent, or Firm*—Peter F. Corless; Christine C. O'Day; Dike, Bronstein, Roberts and Cushman, Intellectual Property Practice Group

(57) ABSTRACT

The present invention relates to a microgranule prepared by using an alkali compound as a stabilizer for a 5-pyrrolyl-2-pyridylmethylsulfinylbenzimidazole derivative having the following formula (1), which is a very effective antiulcerative but highly unstable under acidic conditions, and by using a water-soluble polymer as a binding agent.

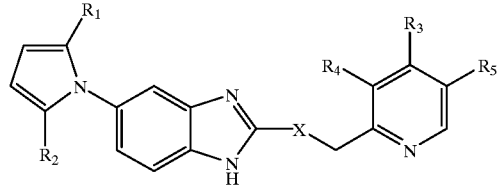

(1)

in which
X, $R_1$, $R_2$, $R_3$, $R_4$ and $R_5$ are defined as described in the specification.

6 Claims, No Drawings

OPTIMALLY STABILIZED MICROGRANULE COMPRISING 5-PYRROLYL-2-PYRIDYLMETHYLSULFINYLBENZIMIDAZOLE DERIVATIVE

TECHNICAL FIELD

The present invention relates to a microgranule prepared by using an alkali compound as a stabilizer for a 5-pyrrolyl-2-pyridylmethylsulfmylbenzimidazole derivative having the following formula (1), which is a very effective antiulcerative but highly unstable under acidic conditions, and by using a water-soluble polymer as a binding agent.

(1)

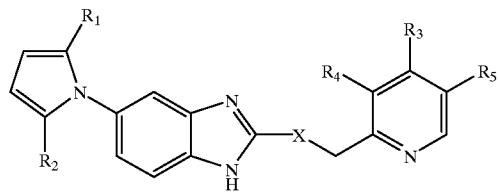

in which
X represents S, SO or $SO_2$,
$R_1$ and $R_2$ independently of one another represent hydrogen or alkyl,
$R_3$ represents hydrogen, $C_1$–$C_8$-alkyl, —$SR_6$, —$N(R_7)_2$, 1-piperidinyl, 4-morpholinyl, 4-methylpiperazin-1-yl, 1-pyrrolidinyl, or a group of general formula —$OR_6$ or —$O(CH_2)_m$—Z,
wherein
$R_6$ represents $C_1$–$C_4$-alkyl, $C_2$–$C_4$-alkenyl, optionally substituted $C_3$–$C_{10}$-cycloalkyl, $C_2$–$C_5$-fluoroalkyl, or phenyl or benzyl each of which is optionally substituted by one or more halogen, or $C_1$–$C_4$-alkyl or alkoxy each of which is optionally substituted by halogen,
$R_7$ represents hydrogen or $C_1$–$C_5$-alkyl,
Z represents a group of general formula —$O(CH_2)_p$—$OR_8$, —$O(CH_2)_q$—$R_9$ or —$O(CH_2)_r O(CH_2)_s$—$OR_{10}$, wherein p and q independently of one another represent an integer of 1 to 3, r and s independently of one another represent an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl,
m represents an integer of 2 to 10,
$R_4$ and $R_5$ independently of one another represent hydrogen or $C_1$–$C_5$-alkyl, or
$R_4$ and $R_3$ or $R_3$ and $R_5$ represent —CH=CH—CH=CH—, —$O(CH_2)_n$—, —$O(CH_2)_nO$—, —$CH_2(CH_2)_n$— or —OCH=CH— when $R_4$ or $R_5$ together with the adjacent carbon atoms on the pyridine ring form a ring, wherein n represents an integer of 1 to 4.

BACKGROUND ART

The 5-pyrrolyl-2-pyridylmethylsulfinylbenzimidazole derivative of formula (1), as defined above, is a novel compound developed by the present inventors, and applications for approval as a product patent are presently pending or granted in 17 countries including Korea, Japan, the United States, etc. It acts as a proton pump inhibitor like the widely known omeprazole, lansoprazole, etc., but is very unstable under acidic or neutral conditions, which may cause several problems in formulation processes.

The 5-pyrrolyl-2-pyridylmethylsulfinylbenzimidazole derivative (in the present specification, it is referred to as 'the active ingredient of the present invention') is very stable under alkali conditions of pH 7.6 or more, and yet it has a half time of 40 minutes or less under acidic conditions (about pH 4.0) and has a half time of 35 hours at neutral conditions (pH 7.0). Therefore, it has been recognized as more unstable under acidic or neutral conditions than omeprazole or lansoprazole which is also unstable under the same condition. Such unstability may cause many problems during storage or distribution. Particularly, it is desired to adjust the ambient circumstance to a low temperature of 4° C. or less, anhydrous and alkaline condition since the degradation of the active ingredient of the present invention is highly facilitated by the moisture and acidic conditions when the storage or distribution temperature becomes 40° C. or more.

The general way for stabilizing the acid-unstable substances is to make an alkaline environment as well as to intercept the influx of moisture from the ambient. But, the present inventors have found that the desired stabilizing effect can hardly be obtained by simply mixing the acid-unstable active ingredient of the present invention with an alkali compound.

Thus, the present inventors have extensively studied to establish a method through which the active ingredient of the present invention can be stablized in a form of microgranule. As a result, we found that such a microgranule can be prepared by combining an alkali compound with the active ingredient of the present invention in a specific mole ratio to adjust the acidity and simultaneously by using a water-soluble polymer as a binding agent in a specific content, and then completed the present invention. Particularly, we have noticed as a result of intensive researches that a certain alkaline salt, that is magnesium hydroxide, among the known alkali compounds, is highly appropriate for stabilizing the active ingredient of the present invention.

DISCLOSURE OF THE INVENTION

Therefore, the present invention provides a microgranule comprising a 5-pyrrolyl-2-pyridylmethylsulfinylbenzimidazole derivative which is optimally stabilized. More specifically, the present invention provides a microgranule prepared by combining a 5-pyrrolyl-2-pyridylmethylsulfinylbenzimidazole derivative of formula (1) with an alkali compound in 0.2 to 7.0 times molar amount with respect to the active ingredient, and by using a water-soluble polymer as a binding agent in 0.1 to 50% by weight with respect to the granule.

In the present specification, the term "microgranule" is used in a meaning that it is not the conventional granule having an average diameter of 1.5 mm or more. Such a microgranule form can be advantageously used when the active ingredient of the present invention is stored or distributed as a medicinal stuff.

DETAILED DESCRIPTION OF THE INVENTION

The alkali compounds which can be used for stabilizing the active ingredient of the present invention in the microgranule according to the present invention include magnesium oxide, sodium phosphate (dibasic), potassium phosphate (dibasic), magnesium hydroxide, magnesium carbonate, aluminum hydroxide, aluminum carbonate, calcium carbonate, sodium carbonate, sodium hydrogen carbonate, potassium carbonate, potassium hydrogen carbonate, aluminum phosphate, calcium phosphate, sodium phosphate, potassium phosphate, aluminum citrate, calcium citrate, sodium citrate, potassium citrate, complexed aluminum/magnesium compound ($Al_2O_3 \cdot 6MgO \cdot 12H_2O$ or $MgO \cdot Al_2O_3 \cdot 2SiO_2 \cdot nH_2O$), arginine, lysine and histidine. These stabilizers contribute to the stability of the acid-unstable active ingredient by maintaining the ambient pH of 7 to 13. However, their contribution degrees to the stability are different from each other depending on their solubility, alkaline reaction efficiency, compatability with the active ingredient, etc. Unexpectedly, it has been identified that magnesium hydroxide exhibits a superior stabilizing effect upon the active ingredient of the present invention compared with the other stabilizers (see, Examples 1 and 2). In contrast, aluminum hydroxide, lysine, etc. have a much less stabilizing effect than magnesium hydroxide although they also have a considerable effect when compared with the control. The present inventors have tested the stabilizing effect for the active ingredient of the present invention using omeprazole, which similarly has an acid-unstable property, as a comparative substance. As a result, it has been recognized that the difference in stabilizing effect depending on the kind of stabilizer is more conspicuous in the active ingredient of the present invention than in omeprazole.

The alkali compound as a stabilizer may be used in 0.2 to 7.0 times molar amount with respect to the active ingredient of the present invention. Although there are some differences according to the kind of stabilizer, this is because the stabilizing effect is trivial in an amount of less than 0.2 times molar amount, and the increased hygroscopicity of the stabilizer may act as an obstacle for the formulation in an amount of more than 7.0 times molar amount. More preferably, the stabilizer is used in an amount of 0.5 to 5.0 times molar amount for convenience' sake in formulation and for excellent stabilizing effect.

The stabilizer may be combined with the active ingredient using a binding agent to prepare the microgranule according to the present invention. The binding agent used herein should be water-soluble and represent neutral to weak acidic property in a solution. Some other coating materials or binding agents may produce acidic conditions, and use of them may cause the decomposition of the active ingredient of the present invention. Therefore, it is required to carefully select the binding agent. As the binding agent which can be preferably used in the present invention, water-soluble polymers, such as for example, hydroxy-methylcellulose, hydroxyethylcellulose, hydroxypropylcellulose, hydroxypropylmethylcellulose, sodium alginate, alginic acid, carbopols$^R$ (carbomer, carboxyvinyl polymer), carboxymethylcellulose, methylcellulose, agar, carrageenan, pectin, guar gum, locust bean gum, xanthan gum, gellan gum, arabic gum, etc. are mentioned.

The binding agent is suitably used in an amount of 0.1 to 50% by weight with respect to the total granule since the granule formation becomes impossible when the binding agent is used in an amount of less than 0.1% by weight, and since the content of the active ingredient in the final formulation becomes too small and substantial coating effect, which is not desired by the present inventors, may be produced in an amount of more than 50% by weight.

The preparation of the microgranule may be carried out by using a conventional granulator, CF-granulator or fluidized-bed granulator. The conventional granulator has several problems, however, that it requires much time for granulation, dryness, etc.; color change of the granule surface is observed due to the continuous contact with the moisture during the dryness; and the like. Therefore, it is more advantageous to use a fluidized-bed granulator or a CF-granulator in view of the stability of the active ingredient or of the prevention of color change, decomposition and content decrease. Particularly, a stable granule can be obtained by using the fluidized-bed granulator since the moisture contained in the binding agent can be eliminated in a short time, and thus it is possible to produce a uniform particle.

The microgranule obtained according to the present invention has been identified as having an excellent stability during the storage and distribution under hot and humid conditions.

The present invention will be more specifically explained by the following examples. However, it should be understood that the examples are intended to illustrate but not to in any manner limit the scope of the present invention. In the following examples, IY-81149 represents the compound of formula (1) wherein X is sulfinyl(S=O), each of $R_1$, $R_2$ and $R_5$ is hydrogen, $R_3$ is methoxy, and $R_4$ is methyl (see, the following formula):

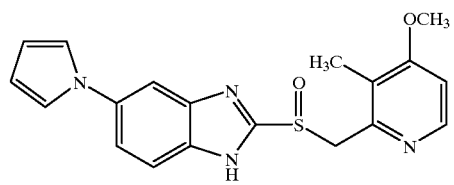

EXAMPLE 1

Stability of the Active Ingredient Depending on the Stabilizer

Each of the active ingredient of the present invention (IY-81149) and the known omeprazole was mixed with the alkali compound shown in the following Table 1 in a mole ratio of 1:1, respectively. That is, 159.2 mg of $Mg(OH)_2$, 387.7 mg of $Na_2HPO_4$, 475.6 mg of $K_2HPO_4$, 229.3 mg of $NaHCO_3$, 289.4 mg of $Na_2CO_3$, 377.3 mg of $K_2CO_3$, 273.3 mg of $KHCO_3$, 212.9 mg of $Al(OH)_3$, 475.6 mg of arginine, 423.7 mg of histidine or 399.1 mg of lysine was mixed with 1.0 g of the active ingredient, and then stored for 15 days under an accelerative condition (40° C., relative humidity of 75%). Then, the content of the active ingredient not decomposed was analyzed using a high performance liquid chromatography. The sample containing only the active ingredient without a stabilizer was used as a control. The analyzing conditions were represented in the following, and the results are shown in Table 1.

<Conditions for High Performance Liquid Chromatography>

Column: $\mu$-Bondapak C18 (4.6×250 mm) or the like
Detector: Absorption photometer in ultraviolet part (wavelength: 280 nm)
Mobile Phase: acetonitrile/phosphate buffer (pH 7.8)=45/55, v/v
Flow Rate: 1.0 ml/min
Injection Amount: 20 $\mu$l

TABLE 1

Stability of the active ingredient depending on the stabilizer

| Stabilizer | Molecular Weight | Mole Ratio | Water-Solubility (g/ml) | Content of the Active Ingredient (%) (IY-81149) Initial | Content of the Active Ingredient (%) (IY-81149) After 15 days | Content of the Active Ingredient (%) (Omeprazole) Initial | Content of the Active Ingredient (%) (Omeprazole) After 15 days |
|---|---|---|---|---|---|---|---|
| not used | — | — | — | 100.1 | 12.6 | 99.3 | 26.7 |
| $Mg(OH)_2$ | 58.3 | 1:1 | 1/80,000 | 99.8 | 93.5 | 100.2 | 86.1 |
| $Na_2HPO_4$ | 142.0 | 1:1 | 1/8 | 99.2 | 82.1 | 99.8 | 94.0 |
| $K_2HPO_4$ | 174.2 | 1:1 | 1/0.67 | 100.0 | 74.2 | 99.4 | 70.7 |
| $NaHCO_3$ | 84.0 | 1:1 | 1/10 | 98.9 | 78.0 | 99.7 | 87.5 |
| $Na_2CO_3$ | 106.0 | 1:1 | 1/3.5 | 99.4 | 79.9 | 100.1 | 75.3 |
| $K_2CO_3$ | 138.2 | 1:1 | 1/1 | 100.5 | 63.4 | 100.0 | 63.9 |
| $KHCO_3$ | 100.1 | 1:1 | 1/2.8 | 100.3 | 65.3 | 99.9 | 59.4 |
| $Al(OH)_3$ | 78.0 | 1:1 | 1/10,000 | 99.6 | 50.7 | 99.6 | 67.6 |
| Arginine | 174.2 | 1:1 | 1/6.67 | 99.2 | 75.5 | 99.1 | 76.0 |
| Histidine | 155.2 | 1:1 | 1/23.9 | 100.6 | 66.2 | 99.7 | 67.1 |
| Lysine | 146.2 | 1:1 | less than 1/1 | 100.6 | 58.8 | 99.2 | 60.3 |

The results of the above Table 1 provide a very important information which can be referred to in selecting the alkali compound as a stabilizer for the active ingredient of the present invention. The data let us know that the tested stabilizers show a stabilizing effect with respect to the active ingredient of the present invention in the order of $Mg(OH)_2$>$Na_2HPO_4$>$Na_2CO_3$>$NaHCO_3$>arginine>$K_2HPO_4$>histidine>$KHCO_3$>$K_2CO_3$>lysine>$Al(OH)_3$ when compared with the control group. Particularly, since magnesium hydroxide shows a 11% more excellent stabilizing effect than $Na_2HPO_4$, the secondary effective stabilizer, it is recognized that magnesium hydroxide is a selectively excellent stabilizer for the active ingredient of the present invention. On the other hand, in the case of the known omeprazole, the tested stabilizers show a stabilizing effect in the order of $Na_2HPO_4$>$NaHCO_3$>$Mg(OH)_2$>arginine>$Na_2CO_3$>$K_2HPO_4$>$Al(OH)_3$>histidine>$K_2CO_3$>lysine>$KHCO_3$. Therefore, such results suggest that the same alkali compound may exhibit a different stabilizing effect depending on the active ingredient to be stabilized and that magnesium hydroxide is particularly suitable for the active ingredient of the present invention.

Further, the results represented in Table 1 suggest that the water-solubility (i.e., hygroscopicity) and alkalizing ability of the stabilizers have some close relation with the stabilizing ability thereof. Thus, it can be seen that one of the essential aspects to be considered when a stabilizer for a certain compound is selected is the water-solubility of the stabilizer.

EXAMPLE 2
Determination of Suitable Amount of the Stabilizer

After the stabilizer is selected based on the results of Table 1, the suitable amount to be used should be determined. Therefore, in order to determine the suitable amount, the present inventors mixed the active ingredient of the present invention (IY-81149) with the respective stabilizers in ratios represented below, and then stored the mixtures for 15 days under an accelerative condition (40° C., relative humidity of 75%). Then, the content of the active ingredient was analyzed according to the same manner as Example 1. The results are shown in the following Table 2.

1) $Mg(OH)_2$: 31.8 mg (Mole ratio 1:0.2), 79.6 mg (Mole ratio 1:0.5), 159.2 mg (Mole ratio 1:1), 318.3 mg (Mole ratio 1:2), 795.8 mg (Mole ratio 1:5) and 1114.1 mg (Mole ratio 1:7) per 1.0 g of the active ingredient of the present invention;

2) $Na_2HPO_4$: 77.5 mg (Mole ratio 1:0.2), 193.8 mg (Mole ratio 1:0.5), 387.7 mg (Mole ratio 1:1), 775.3 mg (Mole ratio 1:2), 1938.3 mg (Mole ratio 1:5) and 2713.6 mg (Mole ratio 1:7) per 1.0 g of the active ingredient of the present invention;

3) $K_2HPO_4$: 95.1 mg (Mole ratio 1:0.2), 237.8 mg (Mole ratio 1:0.5), 475.6 mg (Mole ratio 1:1), 951.1 mg (Mole ratio 1:2), 2377.8 mg (Mole ratio 1:5) and 3329.0 mg (Mole ratio 1:7) per 1.0 g of the active ingredient of the present invention;

4) $NaHCO_3$: 45.9 mg (Mole ratio 1:0.2), 114.7 mg (Mole ratio 1:0.5), 229.3 mg (Mole ratio 1:1), 458.6 mg (Mole ratio 1:2), 1146.6 mg (Mole ratio 1:5) and 1605.2 mg (Mole ratio 1:7) per 1.0 g of the active ingredient of the present invention;

5) $Na_2CO_3$: 57.9 mg (Mole ratio 1:0.2), 144.7 mg (Mole ratio 1:0.5), 289.4 mg (Mole ratio 1:1), 578.8 mg (Mole ratio 1:2), 1446.9 mg (Mole ratio 1:5) and 2025.7 mg (Mole ratio 1:7) per 1.0 g of the active ingredient of the present invention;

6) $K_2CO_3$: 75.5 mg (Mole ratio 1:0.2), 188.6 mg (Mole ratio 1:0.5), 377.3 mg (Mole ratio 1:1), 754.6 mg (Mole ratio 1:2), 1886.4 mg (Mole ratio 1:5) and 2641.0 mg (Mole ratio 1:7) per 1.0 g of the active ingredient of the present invention;

7) $KHCO_3$: 54.7 mg (Mole ratio 1:0.2), 136.6 mg (Mole ratio 1:0.5), 273.3 mg (Mole ratio 1:1), 546.5 mg (Mole ratio 1:2), 1366.4 mg (Mole ratio 1:5) and 1912.9 mg (Mole ratio 1:7) per 1.0 g of the active ingredient of the present invention;

8) $Al(OH)_3$: 42.6 mg (Mole ratio 1:0.2), 106.5 mg (Mole ratio 1:0.5), 212.9 mg (Mole ratio 1:1), 425.9 mg (Mole ratio 1:2), 1064.7 mg (Mole ratio 1:5) and 1490.6 mg (Mole ratio 1:7) per 1.0 g of the active ingredient of the present invention;

9) Arginine: 95.1 mg (Mole ratio 1:0.2), 237.8 mg (Mole ratio 1:0.5), 475.6 mg (Mole ratio 1:1), 951.1 mg (Mole ratio 1:2), 2377.8 mg (Mole ratio 1:5) and 3329.0 mg (Mole ratio 1:7) per 1.0 g of the active ingredient of the present invention;

10) Histidine: 84.7 mg (Mole ratio 1:0.2), 211.8 mg (Mole ratio 1:0.5), 423.7 mg (Mole ratio 1:1), 847.4 mg (Mole ratio 1:2), 2118.5 mg (Mole ratio 1:5) and 2793.9 mg (Mole ratio 1:7) per 1.0 g of the active ingredient of the present invention;

11) Lysine: 79.8 mg (Mole ratio 1:0.2), 199.6 mg (Mole ratio 1:0.5), 399.1 mg (Mole ratio 1:1), 798.3 mg (Mole ratio 1:2), 1995.6 mg (Mole ratio 1:5) and 2793.9 mg (Mole ratio 1:7) per 1.0 g of the active ingredient of the present invention.

TABLE 2

Stability of the active ingredient depending on the mixing ratio with the stabilizer

| Stabilizer | Content of the Active Ingredient (%) after 15 days | | | | | |
|---|---|---|---|---|---|---|
| | Mole ratio of 1:0.2 | Mole ratio of 1:0.5 | Mole ratio of 1:1 | Mole ratio of 1:2 | Mole ratio of 1:5 | Mole ratio of 1:7 |
| $Mg(OH)_2$ | 65.7 | 87.2 | 93.5 | 97.0 | 93.3 | 90.0 |
| $Na_2HPO_4$ | 56.0 | 76.8 | 82.1 | 88.4 | 80.2 | 73.3 |
| $K_2HPO_4$ | 78.4 | 67.4 | 74.2 | 73.5 | 64.7 | 52.6 |
| $NaHCO_3$ | 58.5 | 72.1 | 78.0 | 80.8 | 77.6 | 72.5 |
| $Na_2CO_3$ | 51.2 | 68.0 | 79.9 | 84.2 | 70.0 | 66.2 |
| $K_2CO_3$ | 37.9 | 56.7 | 63.4 | 64.0 | 54.5 | 47.1 |
| $KHCO_3$ | 40.8 | 58.5 | 65.3 | 68.4 | 62.7 | 53.3 |

TABLE 2-continued

Stability of the active ingredient depending on the mixing ratio with the stabilizer

| | Content of the Active Ingredient (%) after 15 days | | | | | |
|---|---|---|---|---|---|---|
| Stabilizer | Mole ratio of 1:0.2 | Mole ratio of 1:0.5 | Mole ratio of 1:1 | Mole ratio of 1:2 | Mole ratio of 1:5 | Mole ratio of 1:7 |
| Al(OH)$_3$ | 27.6 | 38.3 | 50.7 | 53.1 | 53.5 | 52.9 |
| Arginine | 51.0 | 66.9 | 75.5 | 77.3 | 69.4 | 68.4 |
| Histidine | 38.2 | 55.4 | 66.2 | 68.5 | 67.1 | 61.5 |
| Lysine | 34.6 | 51.7 | 58.8 | 47.1 | 42.7 | 43.8 |

The results of Table 2 show that the water-solubility of a stabilizer has a close relation with the stability of the active ingredient. That is, the water-solubility of a stabilizer is related to the hygroscopic property of the stabilizer, which in turn exerts a considerable influence on the stability of the active ingredient since the ingredient is very sensitive to the ambient moisture. Therefore, the amount of the stabilizer to be used should be determined upon considering the hygroscopicity of the stabilizer.

From the results of Table 2, it can be seen that the suitable amount of the stabilizer based on its water-solubility ranges from 0.2 to 7.0 times molar amount with respect to the active ingredient of the present invention since the desired stabilizing effect cannot be obtained in an amount of less than 0.2 times molar amount, and the increased hygroscopicity of the stabilizer may act as an obstacle for the formulation in an amount of more than 7.0 times molar amount.

EXAMPLE 3
Preparation of Microgranule Using Water-Soluble Polymer as a Binding Agent Microgranules were prepared according to the information represented in the following Table 3 using the stabilizers in a mole ratio of 1:1 with respect to the active ingredient (IY-81149) and using hydroxypropylmethylcellulose as a binding agent. A fluidized-bed granulator (SFC-MINI, FREUND. CO., LTD., Japan) by which the contact with the ambient moisture can be excluded and preparation and dryness of the granule can be simultaneously carried out in a short time was used. That is, the active ingredient and stabilizer were introduced into a chamber of the fluidized-bed granulator in the amounts shown in Table 3. Then, the binding agent-containing solution was sprayed under the influx air temperature (65° C.) of the chamber, during which the mixture of the active ingredient and stabilizer in the chamber was maintained at a temperature of 40° C. or less. The binding agent was used in an amount of 7% by weight with respect to the granule finally obtained, and the solvent water was used in an amount to dilute the binding agent by 15 times. Also, the total amount of the active ingredient and stabilizer to be introduced into the chamber was adjusted to 300 g. The average particle diameter of the microgranule prepared by appropriately controlling the spray rate and temperature was 0.8 mm. This granule was stored for 15 days and 8 weeks, respectively, under an accelerative condition (40° C., relative humidity of 75%). Then, the content of the active ingredient was analyzed according to the same manner as Example 1. The results are shown in the following Table 3.

TABLE 3

Composition and stability of the microgranule prepared in the presence of a binding agent (Unit: g)

| Component | | Control granule | A | B | C | D | E | F | G | H | I | J | K |
|---|---|---|---|---|---|---|---|---|---|---|---|---|---|
| Active Ingredient (IY-81149) | | 300 | 258.9 | 216.2 | 203.3 | 244.0 | 232.7 | 217.8 | 235.6 | 247.3 | 203.3 | 210.7 | 214.4 |
| Stabilizer | | — | 41.1 | 83.8 | 96.7 | 56.0 | 67.3 | 82.2 | 64.4 | 52.7 | 96.7 | 89.3 | 85.6 |
| Binding Agent | Hydroxy propyl methyl cellulose | 22.6 | 22.6 | 22.6 | 22.6 | 22.6 | 22.6 | 22.6 | 22.6 | 22.6 | 22.6 | 22.6 | 22.6 |
| Solvent | Distilled Water (ml.) | 340 | 340 | 340 | 340 | 340 | 340 | 340 | 340 | 340 | 340 | 340 | 340 |
| Initial Content (%) | | 99.7 | 100.3 | 99.6 | 100.1 | 99.2 | 99.0 | 100.0 | 99.7 | 99.8 | 99.5 | 99.9 | 100.1 |
| Content of the Active Ingredient (%) after 15 days | | 25.7 | 95.9 | 87.0 | 79.6 | 83.2 | 85.3 | 68.4 | 70.9 | 57.2 | 77.3 | 71.5 | 64.0 |
| Content of the Active Ingredient (%) after 8 weeks | | 14.8 | 86.5 | 68.7 | 58.1 | 63.3 | 60.7 | 45.9 | 55.0 | 48.2 | 65.0 | 51.4 | 49.8 |

It can be seen from the results of Table 3 that using a binding agent to closely contact the active ingredient with the stabilizer, rather than simply mixing the active ingredient with the stabilizer, contributes to the synergistic stabilization of the active ingredient. Also, the binding agent is proven to exhibit a kind of coating effect, which optimizes the stability of the active ingredient. Therefore, it is expected that such a granule form through which the stability of the active ingredient of the present invention is optimized may be utilized very advantageously when it is industrially stored or distributed at room temperature.

Further, the above results also indicate that magnesium hydroxide shows a superior stabilizing effect to the other stabilizers.

What is claimed is:

1. A granule comprising a 5-pyrrolyl-2-pyridylmethylsulfinylbenzimidazole derivative represented by the following formula (1):

(1)

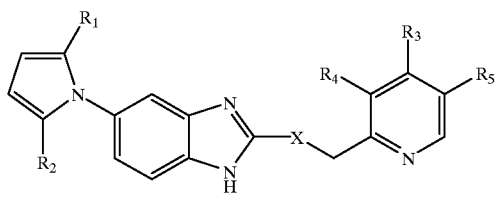

in which

X represents S, SO or $SO_2$, $R_1$ and $R_2$ independently of one another represent hydrogen or alkyl, $R_3$ represents hydrogen, $C_1$–$C_8$-alkyl, —$SR_6$, —$N(R_7)_2$, 1-piperidinyl, 4-morpholinyl, 4-methylpiperazin-1-yl, 1-pyrrolidinyl, or a group of general formula —$OR_6$ or —$O(CH_2)_m$—Z, wherein $R_6$ represents $C_1$–$C_4$-alkyl, $C_2$–$C_4$-alkenyl, optionally substituted $C_3$–$C_{10}$-cycloalkyl, $C_2$–$C_5$-fluoroalkyl, or phenyl or benzyl each of which is optionally substituted by one or more halogen, or $C_1$–$C_4$-alkyl or alkoxy each of which is optionally substituted by halogen, $R_7$ represents hydrogen or $C_1$–$C_5$-alkyl, Z represents a group of general formula —$O(CH_2)_p$—$OR_8$, —$O(CH_2)_q$—$R_9$ or —$O(CH_2)_rO(CH_2)_s$—$OR_{10}$, wherein p and q independently of one another represent an integer of 1 to 3, r and s independently of one another represent an integer of 1 to 5, $R_8$ represents hydrogen, lower alkyl, aryl or aralkyl, $R_9$ represents hydrogen, alkoxycarbonyl, aryl or heteroaryl, and $R_{10}$ represents hydrogen or lower alkyl, m represents an integer of 2 to 10, $R_4$ and $R_5$ independently of one another represent hydrogen or $C_1$–$C_5$-alkyl, or $R_4$ and $R_3$ or $R_3$ and $R_5$ represent —CH=CH—CH=CH—, —$O(CH_2)_n$—, —$O(CH_2)_nO$—, —$CH_2(CH_2)_n$— or —OCH=CH— when $R_4$ or $R_5$ together with the adjacent carbon atoms on the pyridine ring form a ring, wherein n represents an integer of 1 to 4 as an active ingredient, an alkali compound as a stabilizer in 0.2 to 7.0 times molar amount with respect to the active ingredient, and a water-soluble polymer as a binding agent in 0.1 to 50% by weight with respect to the granule.

2. The granule of claim 1 wherein the water-soluble polymer is one or more selected from a group consisting of hydroxymethylcellulose, hydroxyethylcellulose, hydroxypropylcellulose, hydroxypropylmethylcellulose, sodium alginate, alginic acid, carboxyvinyl polymer, carboxymethylcellulose, methylcellulose, agar, carrageenan, pectin, guar gum, locust bean gum, xanthan gum, gellan gum and arabic gum.

3. The granule of claim 1 wherein the alkali compound is one or more selected from a group consisting of magnesium oxide, sodium phosphate (dibasic), potassium phosphate (dibasic), magnesium hydroxide, magnesium carbonate, aluminum hydroxide, aluminum carbonate, calcium carbonate, sodium carbonate, sodium hydrogen carbonate, potassium carbonate, potassium hydrogen carbonate, aluminum phosphate, calcium phosphate, sodium phosphate, potassium phosphate, aluminum citrate, calcium citrate, sodium citrate, potassium citrate, complexed aluminum/magnesium compound ($Al_2O_3.6MgO.12H_2O$ or $MgO.Al_2O_3.2SiO_2.nH_2O$), arginine, lysine and histidine.

4. The granule of claim 3 wherein the alkali compound is magnesium hydroxide.

5. The granule of claim 1 wherein the alkali compound is used as a stabilizer in 0.5 to 5.0 times molar amount with respect to the 5-pyrrolyl-2-pyridylmethylsulfinylbenzimidazole derivative of formula (1).

6. The granule of claim 1 wherein the granule is prepared by using a fluidized-bed granulator or a CF-granulator.

* * * * *